United States Patent
Parker et al.

[11] Patent Number: 6,079,838
[45] Date of Patent: Jun. 27, 2000

[54] LIGHT EMITTING PANEL ASSEMBLIES

[75] Inventors: Jeffery R. Parker, Strongsville; Mark D. Miller, Parma; Daniel N. Kelsch, Lakewood, all of Ohio

[73] Assignee: Lumitex, Inc., Strongsville, Ohio

[21] Appl. No.: 08/778,089

[22] Filed: Jan. 2, 1997

Related U.S. Application Data

[62] Division of application No. 08/495,176, Jun. 27, 1995, Pat. No. 5,613,751.

[51] Int. Cl.[7] .................................................. F21V 8/00
[52] U.S. Cl. .................................................. 362/31; 362/26
[58] Field of Search .................................. 362/26, 31, 27, 362/329, 330

[56] References Cited

U.S. PATENT DOCUMENTS

| | | |
|---|---|---|
| 3,043,947 | 7/1962 | Albinger, Jr. . |
| 3,070,913 | 1/1963 | Miller . |
| 3,328,570 | 6/1967 | Balchunas . |
| 3,543,014 | 11/1970 | Bustad . |
| 3,571,585 | 3/1971 | Schermerhorn . |
| 3,752,974 | 8/1973 | Baker et al. . |
| 3,761,703 | 9/1973 | Mund et al. . |
| 3,892,959 | 7/1975 | Pulles . |
| 3,958,113 | 5/1976 | Termohlen . |
| 4,043,636 | 8/1977 | Eberhardt et al. . |
| 4,118,111 | 10/1978 | Laesser . |
| 4,177,501 | 12/1979 | Karlin . |
| 4,183,628 | 1/1980 | Laesser . |
| 4,257,084 | 3/1981 | Reynolds . |
| 4,282,560 | 8/1981 | Kringel et al. . |
| 4,290,093 | 9/1981 | Thompson et al. . |
| 4,446,508 | 5/1984 | Kinzie . |
| 4,573,766 | 3/1986 | Bournay, Jr. et al. . |
| 4,630,895 | 12/1986 | Abdala, Jr. et al. . |
| 4,714,983 | 12/1987 | Lang . |
| 4,729,185 | 3/1988 | Baba . |
| 4,751,615 | 6/1988 | Abrams . |
| 4,763,984 | 8/1988 | Awai et al. . |
| 4,765,701 | 8/1988 | Cheslak . |
| 4,974,122 | 11/1990 | Shaw . |
| 4,975,808 | 12/1990 | Bond et al. . |
| 4,978,952 | 12/1990 | Irwin . |
| 5,005,108 | 4/1991 | Pristash et al. . |
| 5,027,258 | 6/1991 | Schoniger et al. . |
| 5,070,431 | 12/1991 | Kitazawa et al. . |
| 5,093,765 | 3/1992 | Kashima et al. . |
| 5,134,549 | 7/1992 | Yokoyama . |
| 5,136,483 | 8/1992 | Schoniger et al. . |
| 5,207,493 | 5/1993 | Murase et al. . |
| 5,262,928 | 11/1993 | Kashima et al. ........................ 362/31 |
| 5,283,673 | 2/1994 | Murase et al. . |
| 5,307,244 | 4/1994 | Gaudette . |
| 5,339,179 | 8/1994 | Rudusill et al. . |
| 5,349,503 | 9/1994 | Blonder et al. . |
| 5,375,043 | 12/1994 | Tokomaga . |
| 5,390,085 | 2/1995 | Mari-Roca et al. . |
| 5,394,308 | 2/1995 | Watanabe et al. . |
| 5,467,208 | 11/1995 | Kokawa et al. . |
| 5,467,417 | 11/1995 | Nakamura et al. . |
| 5,521,342 | 5/1996 | Barley et al. . |
| 5,576,078 | 11/1996 | Schatz . |
| 5,590,945 | 1/1997 | Simms ........................ 362/27 |
| 5,618,095 | 4/1997 | Kashima et al. ........................ 362/26 |
| 5,671,994 | 9/1997 | Tai et al. ........................ 362/31 |
| 5,711,592 | 1/1998 | Hotta . |

FOREIGN PATENT DOCUMENTS

| | | |
|---|---|---|
| 0453092 | of 1991 | European Pat. Off. . |
| 96/17207 | of 1996 | WIPO . |

*Primary Examiner*—Y. Quach
*Attorney, Agent, or Firm*—Renner, Otto, Boisselle & Sklar, LLP

[57] ABSTRACT

Light emitting panel assemblies include light emitting panel members and one or more light sources positioned/embedded in a light transition area, which increases the efficiency of light entering the panel members along the light input area to be emitted from one or more light emitting surfaces along the length of the panel members. Light may be reflected or refracted by a surface which changes the path of a portion of light such that it enters the input area of the panel member at a more acceptable angle. A uniform light output distribution may be produced by utilizing a pattern of light extracting deformities.

25 Claims, 4 Drawing Sheets

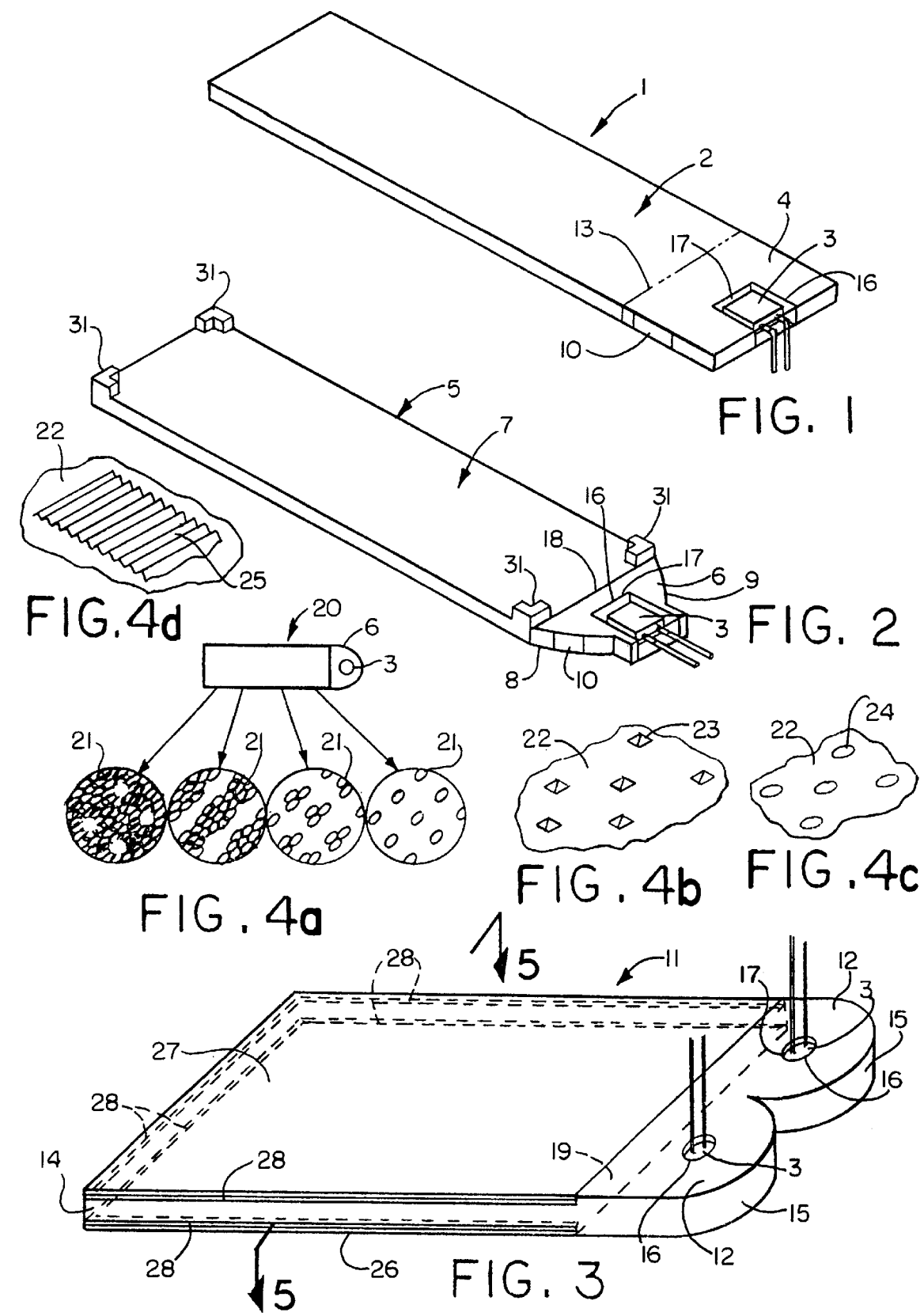

LIGHT EMITTING PANEL ASSEMBLIES

This is a divisional of application(s) Ser. No. 08/495,176 filed on Jun. 27, 1995 now U.S. Pat. No. 5,613,751.

BACKGROUND OF THE INVENTION

This invention relates generally, as indicated, to light emitting panel assemblies each including a transparent panel member for efficiently conducting light, and controlling the light conducted by the panel member to be emitted from one or more light output areas along the length thereof.

Light emitting panel assemblies are generally known. However, the present invention relates to several different light emitting panel assembly configurations which provide for better control of the light output from the panel assemblies and for more efficient utilization of light, which results in greater light output from the panel assemblies.

SUMMARY OF THE INVENTION

In accordance with one aspect of the invention, the light emitting panel assemblies include a light emitting panel member having a light transition area in which at least one light source is suitably mounted for transmission of light to the light input surface of the panel member.

In accordance with another aspect of the invention, the light source is desirably embedded, potted or bonded to the light transition area to eliminate any air gaps, decrease surface reflections and/or eliminate any lens effect between the light source and light transition area, thereby reducing light loss and increasing the light output from the panel assembly.

In accordance with another aspect of the invention, the panel assemblies may include reflective or refractive surfaces for changing the path of a portion of the light, emitted from the light source, that would not normally enter the panel members at an acceptable angle that allows the light to remain in the panel members for a longer period of time and/or increase the efficiency of the panel members.

In accordance with another aspect of the invention, the light emitting panel members include a pattern of light extracting deformities or disruptions which provide a desired light output distribution from the panel members by changing the angle of refraction of a portion of the light from one or more light output areas of the panel members.

In accordance with still another aspect of the invention, the light source may include multiple colored light sources for supplying light to one or more light output areas, and for providing a colored or white light output distribution.

In accordance with yet another aspect of the invention, the panel assemblies include a transition area for mixing the multiple colored lights, prior to the light entering the panel members, in order to effect a desired colored or white light output distribution.

The various light emitting panel assemblies of the present invention are very efficient panel assemblies that may be used to produce increased uniformity and higher light output from the panel members with lower power requirements, and allow the panel members to be made thinner and/or longer, and/or of various shapes and sizes.

To the accomplishment of the foregoing and related ends, the invention then comprises the features hereinafter fully described and particularly pointed out in the claims, the following description and the annexed drawings setting forth in detail certain illustrative embodiments of the invention, these being indicative, however, of but several of the various ways in which the principles of the invention may be employed.

BRIEF DESCRIPTION OF THE DRAWINGS

In the annexed drawings:

FIGS. 1 through 3 are schematic perspective views of three different forms of light emitting panel assemblies in accordance with this invention;

FIG. 4a is an enlarged plan view of a portion of a light output area of a panel assembly showing one form of pattern of light extracting deformities on the light output area;

FIGS. 4b, c and d are enlarged schematic perspective views of a portion of a light output area of a panel assembly showing other forms of light extracting deformities formed in or on the light output area;

DETAILED DESCRIPTION OF THE PREFERRED EMBODIMENTS

Figure 5:
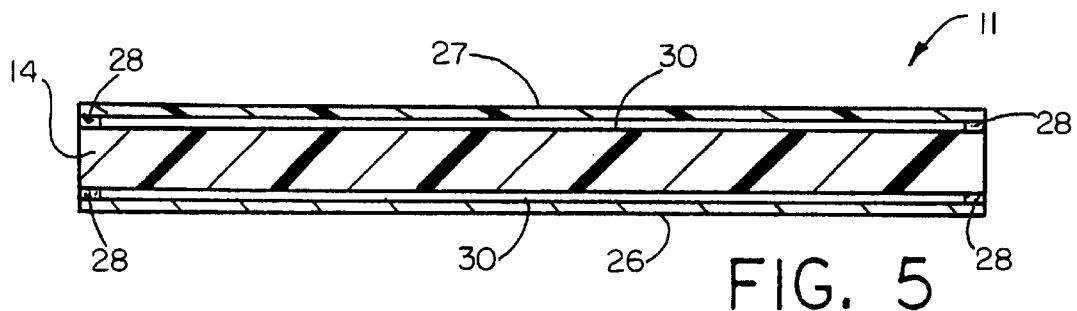
FIG. 5 is an enlarged transverse section through the light emitting panel assembly of FIG. 3 taken generally on the plane of the line 5—5 thereof.

Referring now in detail to the drawings, and initially to FIG. 1, there is schematically shown one form of light emitting panel assembly 1 in accordance with this invention including a transparent light emitting panel 2 and one or more light sources 3 which emit light in a predetermined pattern in a light transition member or area 4 used to make the transition from the light source 3 to the light emitting panel 2, as well known in the art. The light that is transmitted by the light transition area 4 to the transparent light emitting panel 2 may be emitted along the entire length of the panel or from one or more light output areas along the length of the panel as desired to produce a desired light output distribution to fit a particular application.

In FIG. 1 the light transition area 4 is shown as an integral extension of one end of the light emitting panel 2 and as being generally rectangular in shape. However, the light transition area may be of other shapes suitable for embedding, potting, bonding or otherwise mounting the light source. Also, reflective or refractive surfaces may be provided to increase efficiency. Moreover, the light transition area 4 may be a separate piece suitably attached to the light input surface 13 of the panel member if desired. Also, the sides of the light transition area may be curved to more efficiently reflect or refract a portion of the light emitted from the light source through the light emitting panel at an acceptable angle.

FIG. 2 shows another form of light emitting panel assembly 5 in accordance with this invention including a panel light transition area 6 at one end of the light emitting panel 7 with sides 8, 9 around and behind the light source 3 shaped to more efficiently reflect and/or refract and focus the light emitted from the light source 3 that impinges on these surfaces back through the light transition area 6 at an acceptable angle for entering the light input surface 18 at one end of the light emitting panel 7. Also, a suitable reflective material or coating 10 may be provided on the portions of the sides of the light transition areas of the panel assemblies of FIGS. 1 and 2 on which a portion of the light impinges for maximizing the amount of light or otherwise changing the light that is reflected back through the light transition areas and into the light emitting panels.

The panel assemblies shown in FIGS. 1 and 2 include a single light source 3, whereas FIG. 3 shows another light emitting panel assembly 11 in accordance with this invention including two light sources 3. Of course, it will be appreciated that the panel assemblies of the present invention may be provided with any number of light sources as desired, depending on the particular application.

The panel assembly 11 of FIG. 3 includes a light transition area 12 at one end of the light emitting panel 14 having reflective and/or refractive surfaces 15 around and behind each light source 3. These surfaces 15 may be appropriately shaped including for example curved, straight and/or faceted surfaces, and if desired, suitable reflective materials or coatings may be provided on portions of these surfaces to more efficiently reflect and/or refract and focus a portion of the light emitted for example from an incandescent light source which emits light in a 360° pattern through the light transition areas 12 into the light input surface 19 of the light emitting panel 14.

The light sources 3 may be mechanically held in any suitable manner in slots, cavities or openings 16 machined, molded or otherwise formed in the light transition areas of the panel assemblies. However, preferably the light sources 3 are embedded, potted or bonded in the light transition areas in order to eliminate any air gaps or air interface surfaces between the light sources and surrounding light transition areas, thereby reducing light loss and increasing the light output emitted by the light emitting panels. Such mounting of the light sources may be accomplished, for example, by bonding the light sources 3 in the slots, cavities or openings 16 in the light transition areas using a sufficient quantity of a suitable embedding, potting or bonding material 17. The slots, cavities or openings 16 may be on the top, bottom, sides or back of the light transition areas. Bonding can also be accomplished by a variety of methods that do not incorporate extra material, for example, thermal bonding, heat staking, ultrasonic or plastic welding or the like. Other methods of bonding include insert molding and casting around the light source(s).

A transparent light emitting material of any suitable type, for example acrylic or polycarbonate, may be used for the light emitting panels. Also, the panels may be substantially flat, or curved, may be a single layer or multi-layers, and may have different thicknesses and shapes. Moreover, the panels may be flexible, or rigid, and may be made out of a variety of compounds. Further, the panels may be hollow, filled with liquid, air, or be solid, and may have holes or ridges in the panels.

Each light source 3 may also be of any suitable type including, for example, any of the types disclosed in U.S. Pat. Nos. 4,897,771 and 5,005,108, assigned to the same assignee as the present application, the entire disclosures of which are incorporated herein by reference. In particular, the light sources 3 may be an arc lamp, an incandescent bulb which also may be colored, filtered or painted, a lens end bulb, a line light, a halogen lamp, a light emitting diode (LED), a chip from an LED, a neon bulb, a fluorescent tube, a fiber optic light pipe transmitting from a remote source, a laser or laser diode, or any other suitable light source. Additionally, the light sources 3 may be a multiple colored LED, or a combination of multiple colored radiation sources in order to provide a desired colored or white light output distribution. For example, a plurality of colored lights such as LEDs of different colors (red, blue, green) or a single LED with multiple colored chips may be employed to create white light or any other colored light output distribution by varying the intensities of each individual colored light.

A pattern of light extracting deformities or disruptions may be provided on one or both sides of the panel members or on one or more selected areas on one or both sides of the panel members, as desired. FIG. 4a schematically shows one such light surface area 20 on which a pattern of light extracting deformities or disruptions 21 is provided. As used herein, the term deformities or disruptions are used interchangeably to mean any change in the shape or geometry of the panel surface and/or coating or surface treatment that causes a portion of the light to be emitted. The pattern of light extracting deformities 21 shown in FIG. 4a includes a variable pattern which breaks up the light rays such that the internal angle of reflection of a portion of the light rays will be great enough to cause the light rays either to be emitted out of the panel through the side or sides on which the light extracting deformities 21 are provided or reflected back through the panel and emitted out the other side.

These deformities or disruptions 21 can be produced in a variety of manners, for example, by providing a painted pattern, an etched pattern, a machined pattern, a printed pattern, a hot stamped pattern, or a molded pattern or the like on selected light output areas of the panel members. An ink or printed pattern may be applied for example by pad printing, silk screening, ink jet, heat transfer film process or the like. The deformities may also be printed on a sheet or film which is used to apply the deformities to the panel member. This sheet or film may become a permanent part of the light panel assembly for example by attaching or otherwise positioning the sheet or film against one or both sides of the panel member similar to the sheet or film 27 shown in FIGS. 3 and 5 in order to produce a desired effect.

By varying the density, opaqueness or translucence, shape, depth, color, area, index of refraction, or type of deformities 21 on an area or areas of the panels, the light output of the panels can be controlled. The deformities or disruptions may be used to control the percent of light emitted from any area of the panels. For example, less and/or smaller size deformities 21 may be placed on panel areas where less light output is wanted. Conversely, a greater percentage of and/or larger deformities may be placed on areas of the panels where greater light output is desired.

Varying the percentages and/or size of deformities in different areas of the panel is necessary in order to provide a uniform light output distribution. For example, the amount of light traveling through the panels will ordinarily be greater in areas closer to the light source than in other areas further removed from the light source. A pattern of light extracting deformities 21 may be used to adjust for the light variances within the panel members, for example, by providing a denser concentration of light extracting deformities with increased distance from the light source 3 thereby resulting in a more uniform light output distribution from the light emitting panels.

The deformities 21 may also be used to control the output ray angle distribution of the emitted light to suit a particular application. For example, if the panel assemblies are used to provide a liquid crystal display backlight, the light output will be more efficient if the deformities 21 cause the light rays to emit from the panels at predetermined ray angles such that they will pass through the liquid crystal display with low loss.

Additionally, the pattern of light extracting deformities may be used to adjust for light output variances attributed to light extractions of the panel members. The pattern of light extracting deformities 21 may be printed on the light output areas utilizing a wide spectrum of paints, inks, coatings, epoxies, or the like, ranging from glossy to opaque or both, and may employ half-tone separation techniques to vary the deformity 21 coverage. Moreover, the pattern of light extracting deformities 21 may be multiple layers or vary in index of refraction.

Print patterns of light extracting deformities 21 may vary in shapes such as dots, squares, diamonds, ellipses, stars, random shapes, and the like, and are desirably 0.006 square inch per deformity/element or less. Also, print patterns that are 60 lines per inch or finer are desirably employed, thus making the deformities or shapes 21 in the print patterns nearly invisible to the human eye in a particular application thereby eliminating the detection of gradient or banding lines that are common to light extracting patterns utilizing larger elements. Additionally, the deformities may vary in shape and/or size along the length and/or width of the panel members. Also, a random placement pattern of the deformities may be utilized throughout the length and/or width of the panel members. The deformities may have shapes or a pattern with no specific angles to reduce moire or other interference effects. Examples of methods to create these random patterns are printing a pattern of shapes using stochastic print pattern techniques, frequency modulated half tone patterns, or random dot half tones. Moreover, the deformities may be colored in order to effect color correction in the panel members. The color of the deformities may also vary throughout the panel members, for example to provide different colors for the same or different light output areas.

In addition to or in lieu of the patterns of light extracting deformities 21 shown in FIG. 4a, other light extracting deformities including prismatic surfaces, depressions or raised surfaces of various shapes using more complex shapes in a mold pattern may be molded, etched, stamped, thermoformed, hot stamped or the like into or on one or more areas of the panel member. FIGS. 4b and 4c show panel areas 22 on which prismatic surfaces 23 or depressions 24 are formed in the panel areas, whereas FIG. 4d shows prismatic or other reflective or refractive surfaces 25 formed on the exterior of the panel area. The prismatic surfaces, depressions or raised surfaces will cause a portion of the light rays contacted thereby to be emitted from the panel member. Also, the angles of the prisms, depressions or other surfaces may be varied to direct the light in different directions to produce a desired light output distribution or effect. Moreover, the reflective or refractive surfaces may have shapes or a pattern with no specific angles to reduce moire or other interference effects.

As best seen in the cross sectional view of FIG. 5, a back reflector (including trans reflectors) 26 may be attached or positioned against one side of the panel member 14 of FIG. 3 using a suitable adhesive 28 or other method in order to improve light output efficiency of the panel assembly 11 by reflecting the light emitted from that side back through the panel for emission through the opposite side. Additionally, a pattern of light extracting deformities 21, 23, 24 and/or 25 may be provided on one or both sides of the panel member in order to change the path of the light so that the internal critical angle is exceeded and a portion of the light is emitted from one or both sides of the panel. Moreover, a transparent film, sheet or plate 27 may be attached or positioned against the side or sides of the panel member from which light is emitted using a suitable adhesive 28 or other method in order to produce a desired effect.

The member 27 may be used to further improve the uniformity of the light output distribution. For example, the member 27 may be a colored film, a diffuser, or a label or display, a portion of which may be a transparent overlay that may be colored and/or have text or an image thereon.

If adhesive 28 is used to adhere the back reflector 26 and/or film 27 to the panel, the adhesive is preferably applied only along the side edges of the panel, and if desired the end edge opposite the light transition areas 12, but not over the entire surface area or areas of the panel because of the difficulty in consistently applying a uniform coating of adhesive to the panel. Also, the adhesive changes the internal critical angle of the light in a less controllable manner than the air gaps 30 (see FIG. 5) which are formed between the respective panel surfaces and the back reflector 26 and/or film 27 when only adhered along the peripheral edges. Additionally, longer panel members are achievable when air gaps 30 are used. If adhesive were to be used over the entire surface, the pattern of deformities could be adjusted to account for the additional attenuation in the light caused by the adhesive.

Referring further to FIG. 2, the panel assembly 5 shown therein also includes molded posts 31 at one or more corners of the panel 7 (four such posts being shown) which may be used to facilitate mounting of the panel assembly and providing structural support for other parts or components, for example, a display panel such as a liquid crystal display panel as desired.

Figure 6:
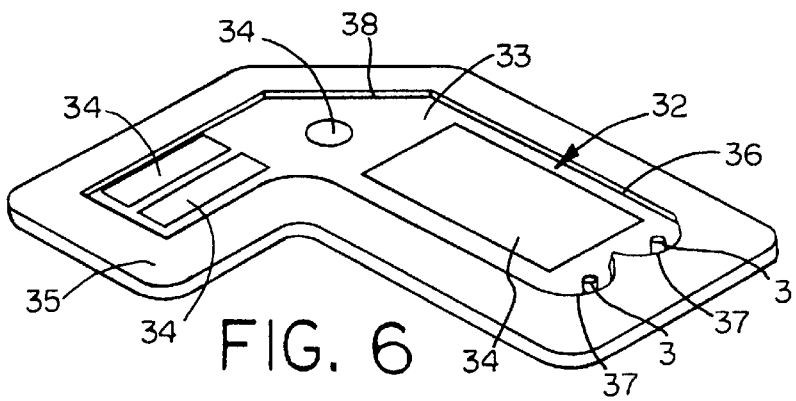
FIG. 6 is a schematic perspective view of another form of light emitting panel assembly in accordance with this invention.

FIG. 6 shows another form of light emitting panel assembly 32 in accordance with this invention including a panel member 33, one or more light sources 3, and one or more light output areas 34. In addition, the panel assembly 32 includes a tray 35 having a cavity or recess 36 in which the panel assembly 32 is received. The tray 35 may act as a back reflector as well as end edge and/or side edge reflectors for the panel 33 and side and/or back reflectors 37 for the light sources 3. Additionally, one or more secondary reflective or refractive surfaces 38 may be provided on the panel member 33 and/or tray 35 to reflect a portion of the light around one or more corners or curves in a non-rectangular shaped panel member 33. These secondary reflective/refractive surfaces 38 may be flat, angled, faceted or curved, and may be used to extract a portion of the light away from the panel member in a predetermined pattern. FIG. 6 also shows multiple light output areas 34 on the panel member that emit light from one or more light sources 3.

Figure 7:
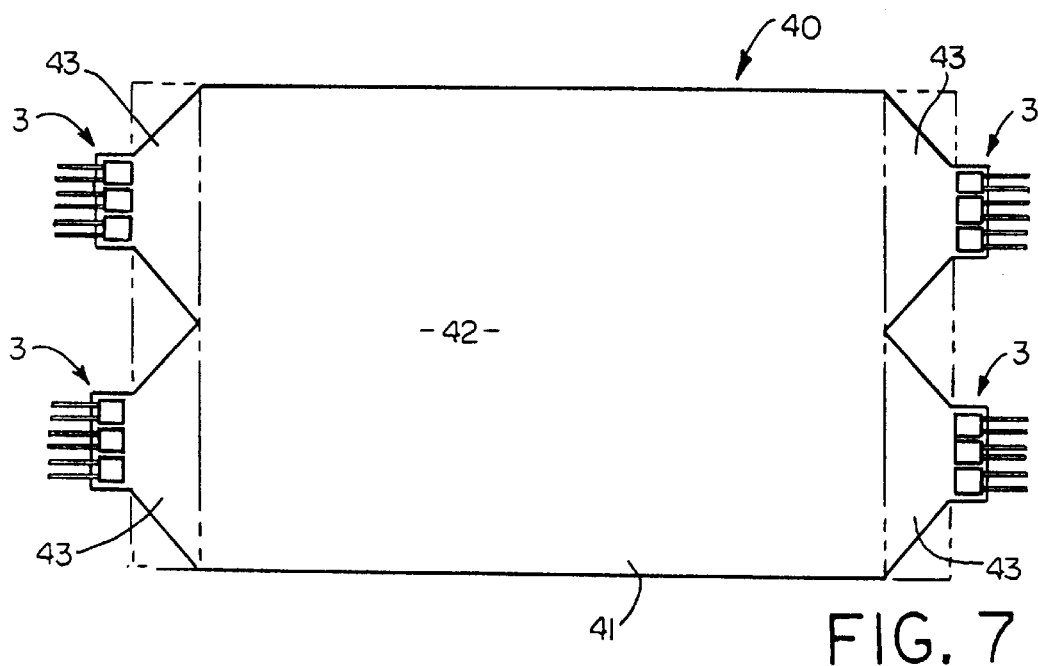
FIG. 7 is a schematic top plan view of another form of light emitting panel assembly in accordance with this invention.

FIG. 7 is a schematic illustration of still another form of light emitting panel assembly 40 in accordance with this invention including a panel member 41 having one or more light output areas 42 and one or more light transition areas (mixing areas) 43 containing a plurality of light sources 3 at one or both ends of the panel. Each transition area mixes the light from one or more light sources having different colors and/or intensities. In this particular embodiment, each of the light sources 3 desirably employs three colored LEDs (red, blue, green) in each transition mixing area 43 so that the light from the three LEDs can be mixed to produce a desired light output color that will be emitted from the light output area 42. Alternatively, each light source may be a single LED having multiple colored chips bonded to the lead film. Also, two colored LEDs or a single LED having two colored chips may be used for a particular application. By varying the intensities of the individual respective LEDs, virtually any colored light output or white light distribution can be achieved.

Figure 8:
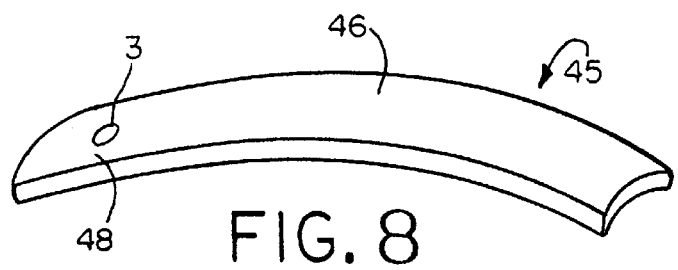
FIG. 8 is a schematic perspective view of another form of light emitting panel assembly in accordance with this invention.

FIG. 8 shows yet another form of light emitting panel assembly 45 in accordance with this invention including a light emitting panel member 46 and a light source 3 in a light transition area 48 integral with one end of the panel member. In this particular embodiment, the panel member 46 is three-dimensionally curved, for example, such that light rays may be emitted in a manner that facilitates aesthetic design of a lighted display.

Figure 9:
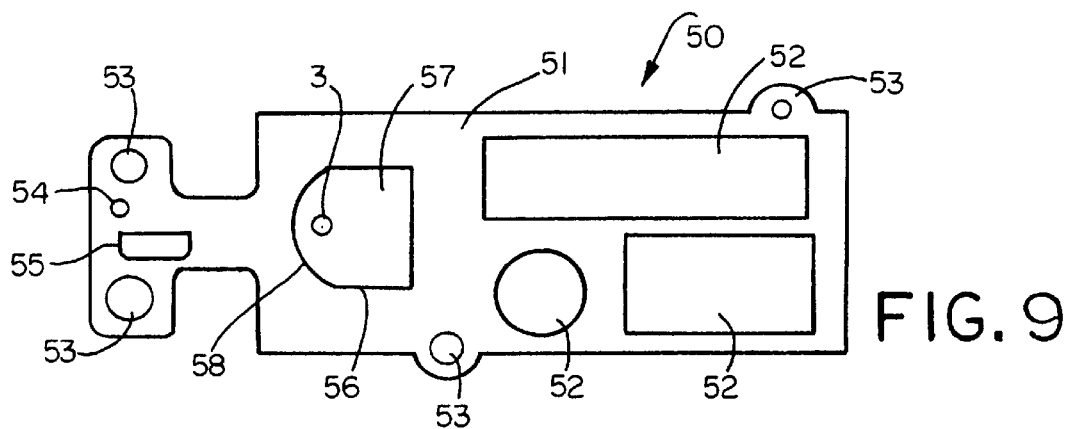
FIG. 9 is a schematic top plan view of another form of light emitting panel assembly in accordance with this invention.

FIG. 9 schematically shows another form of light emitting panel assembly 50 in accordance with this invention, including a panel member 51 having multiple light output areas 52, and mounting posts and/or mounting tabs 53. This particular panel assembly 50 may serve as a structural member to support other parts or components as by providing holes or cavities 54, 55 in the panel member 51 which allow for the insertion of modular components or other parts into the panel member. Moreover, a separate cavity or recess 56 may be provided in the panel member 51 for receipt of a correspondingly shaped light transition area 57 having one or more light sources 3 embedded, bonded, cast, insert molded, epoxied, or otherwise mounted or positioned therein and a curved reflective or refractive surface 58 on the transition area 57 and/or wall of the cavity or recess 56 to redirect a portion of the light in a predetermined manner. In this way the light transition area 57 and/or panel member may be in the form of a separate insert which facilitates the easy placement of the light source in a modular manner. A reflector 58 may be placed on the reflective or refractive surface of the cavity or recess 56 or insert 57. Where the reflector 58 is placed on the reflective or refractive surface of the cavity or recess 56, the cavity or recess may act as a mold permitting transparent material from which the transition area 57 is made to be cast around one or more light sources 3.

Figure 10:
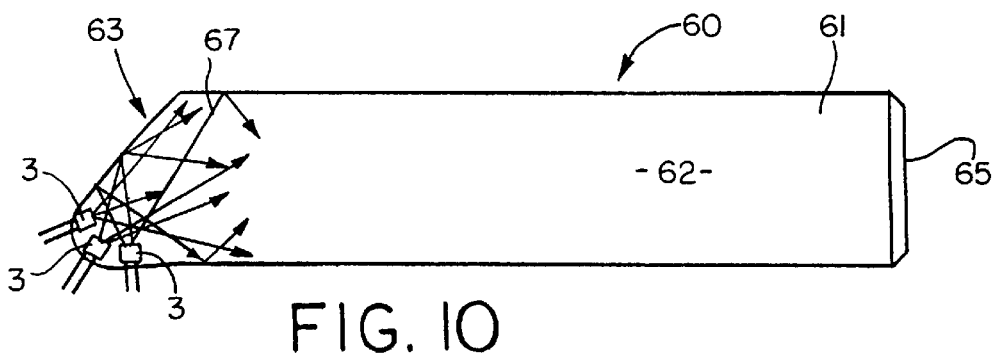
FIG. 10 is a schematic top plan view of still another form of light emitting panel assembly in accordance with this invention.
Figure 11:
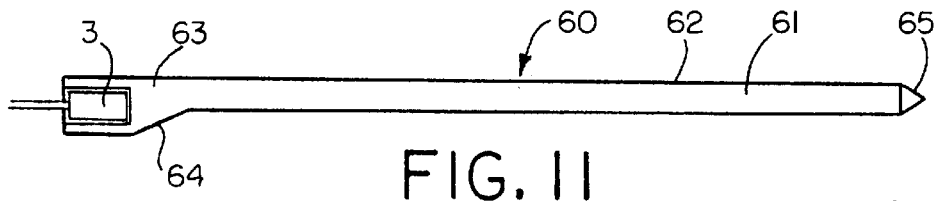
FIG. 11 is a side elevation view of the light emitting panel assembly of FIG. 10.
Figure 11A:
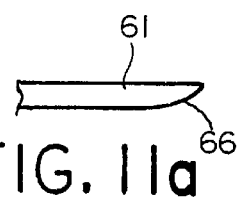
FIG. 11a is a fragmentary side elevation view showing a tapered or rounded end on the panel member in place of the prismatic surface shown in FIGS. 10 and 11.

FIGS. 10 and 11 schematically show another form of light emitting panel assembly 60 in accordance with this invention including a panel member 61 having one or more light output areas 62. In this particular embodiment, an off-axis light transition area 63 is provided that is thicker in cross section than the panel member to permit use of one or more light sources 3 embedded or otherwise mounted in the light transition area that are dimensionally thicker than the panel member. Also, a three-dimensional reflective surface 64 (FIG. 11) may be provided on the transition area 63. Moreover, a prism 65 (FIG. 11) or tapered, rounded, or otherwise shaped end 66 (FIG. 11a) may be provided at the end of the panel opposite the light sources 3 to perform the function of an end reflector. The light sources 3 may be oriented at different angles relative to each other and offset to facilitate better mixing of the light rays 67 in the transition area 63 as schematically shown in FIG. 10 and/or to permit a shorter length transition area 63 to be used.

Figure 12:
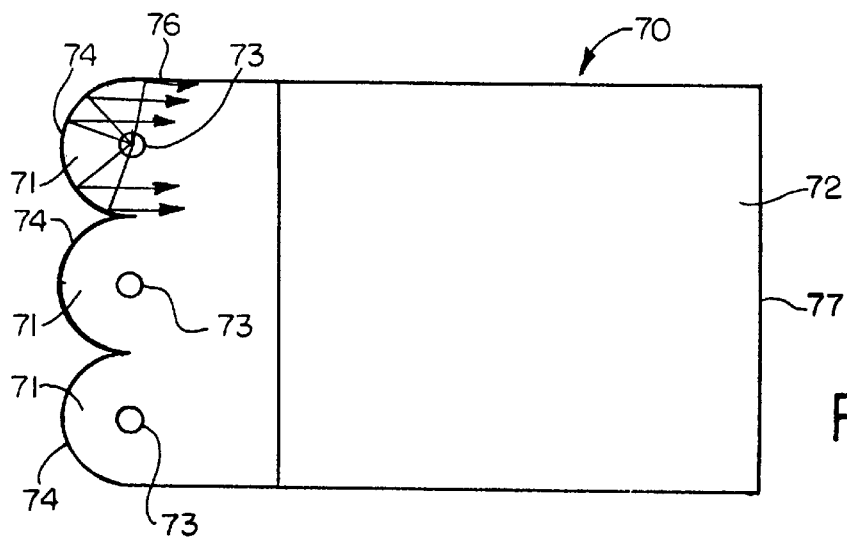
FIG. 12 is a schematic top plan view of another form of light emitting panel assembly in accordance with this invention.
Figure 13:
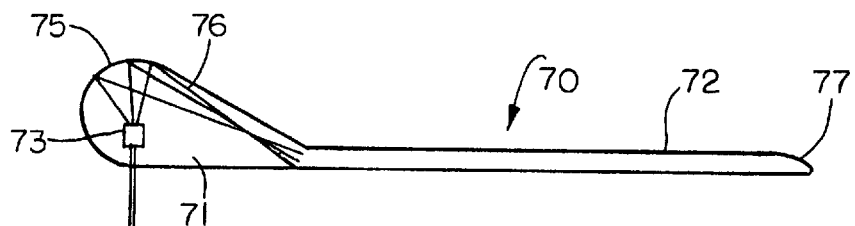
FIG. 13 is a schematic side elevation view of the light emitting panel assembly of FIG. 12.

FIGS. 12 and 13 schematically show still another form of light emitting panel assembly 70 in accordance with this invention which includes one or more light transition areas 71 at one or both ends of the panel member 72 each containing a single light source 73. The transition area or areas 71 shown in FIGS. 12 and 13 collect light with multiple or three-dimensional surfaces and/or collect light in more than one plane. For example each transition area 71 shown in FIGS. 12 and 13 has elliptical and parabolic shape surfaces 74 and 75 in different planes for directing the light rays 76 into the panel member at a desired angle.

Providing one or more transition areas at one or both ends of the panel member of any desired dimension to accommodate one or more light sources, with reflective and/or refractive surfaces on the transition areas for redirecting the light rays into the panel member at relatively low angles allows the light emitting panel member to be made much longer and thinner than would otherwise be possible. For example the panel members of the present invention may be made very thin, i.e., 0.125 inch thick or less.

Figure 14:
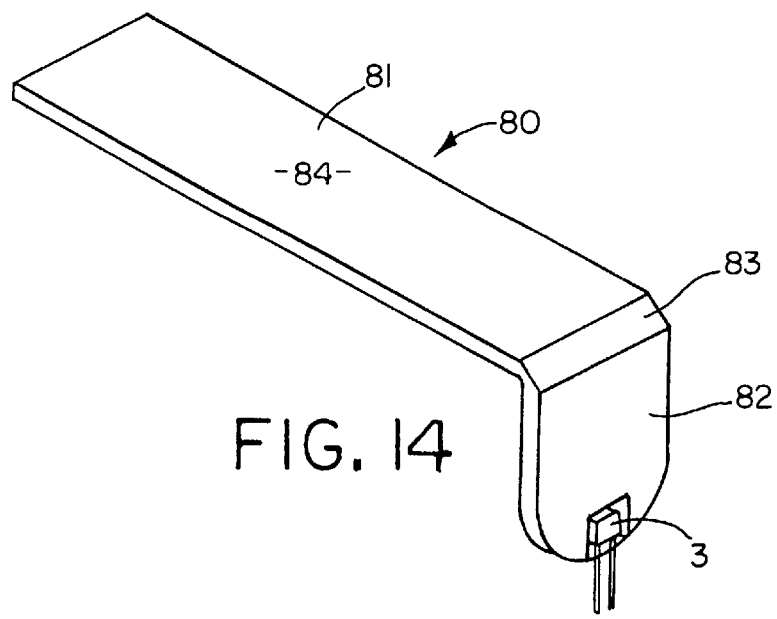
FIGS. 14 and 15 are schematic perspective views of still other forms of light emitting panel assemblies in accordance with this invention.

FIG. 14 schematically illustrates still another form of light emitting panel assembly 80 in accordance with this invention including a light emitting panel 81 and one or more light sources 3 positioned, embedded, potted, bonded or otherwise mounted in a light transition area 82 that is at an angle relative to the panel member 81 to permit more efficient use of space. An angled or curved reflective or refractive surface 83 is provided at the junction of the panel member 81 with the transition area 82 in order to reflect/refract light from the light source 3 into the body of the panel member 81 for emission of light from one or more light emitting areas 84 along the length of the panel member.

Figure 15:
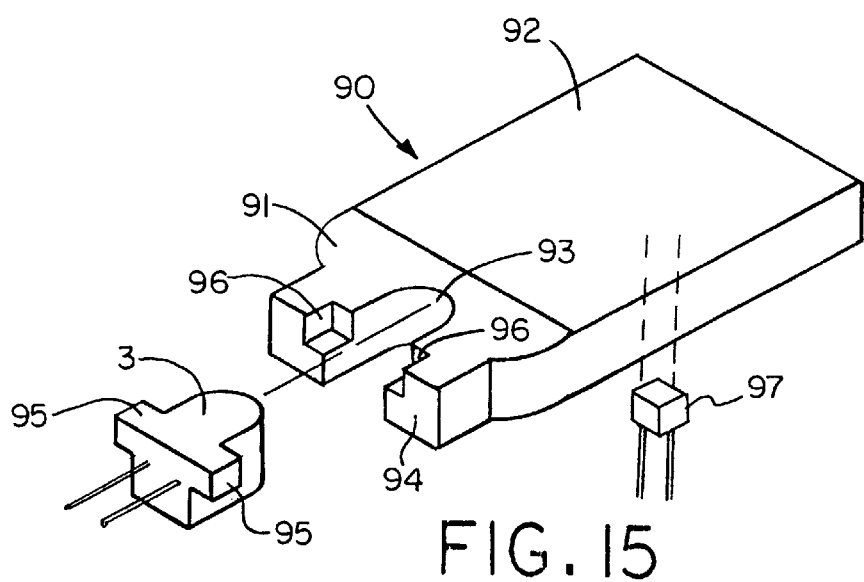

FIG. 15 schematically illustrates still another form of light emitting panel assembly 90 in accordance with this invention including a light transition area 91 at one or both ends of a light emitting panel member 92 containing a slot 93 for sliding receipt of an LED or other suitable light source 3. Preferably the slot 93 extends into the transition area 91 from the back edge 94, whereby the light source 3 may be slid and/or snapped in place in the slot from the back, thus allowing the transition area to be made shorter and/or thinner. The light source 3 may be provided with wings, tabs or other surfaces 95 for engagement in correspondingly shaped recesses or grooves 96 or the like in the transition area 91 for locating and, if desired, securing the light source in place. Also, the light source 3 may be embedded, potted, bonded or otherwise secured within the slot 93 in the light transition area 91 of the panel member 92. Light from a secondary light source 97 may be projected through the panel member 92 for indication or some other effect.

The various light emitting panel assemblies disclosed herein may be used for a great many different applications including for example LCD back lighting or lighting in general, decorative and display lighting, automotive lighting, dental lighting, phototherapy or other medical lighting, membrane switch lighting, and sporting goods and apparel lighting or the like. Also the panel assemblies may be made such that the panel members and deformities are transparent without a back reflector. This allows the panel assemblies to be used for example to front light an LCD or other display such that the display is viewed through the transparent panel members.

Although the invention has been shown and described with respect to certain preferred embodiments, it is obvious that equivalent alterations and modifications will occur to others skilled in the art upon the reading and understanding of the specification. The present invention includes all such equivalent alterations and modifications, and is limited only by the scope of the claims.

What is claimed is:

1. A light emitting panel assembly comprising a light emitting panel member having a greater width than thickness and opposite ends and sides and top and bottom surfaces, a light transition area located at one of said ends, and at least one light source mounted to said light transition area, said panel member having a light input surface at said one end for receiving light from said light transition area, said light input surface having a cross sectional area extending the entire width and thickness of said panel member at said one end, and said light transition area having a light output surface of the same width and thickness as said light input surface at said one end and a reflective surface in close proximity to said light source shaped to cause internal reflection of a portion of the light emitted from said light source and redirect the internally reflected light into said light input surface at said one end to produce a uniform density of light across substantially the entire cross sectional area of said light input surface at said one end, said reflective surface extending around and behind said light source.

2. The assembly of claim 1 wherein said panel member is substantially thin and flat and said reflective surface on said light transition area is shaped to redirect a portion of the light emitted from said light source into said light input surface at said one end of said panel member at a substantially low angle to permit said panel member to be made thinner and longer than would otherwise be possible and still obtain a substantially uniform light output from one of said top and bottom surfaces of said panel member when illuminated from said one end only.

3. The assembly of claim 2 wherein said panel member is no more than 0.125 inch thick.

4. The assembly of claim 1 further comprising a pattern of light extracting deformities on said panel member, said light extracting deformities having a density concentration for causing a substantially uniform light output from one of said top and bottom surfaces of said panel member.

5. The assembly of claim 4 wherein said light extracting deformities are formed by applying a coating on said panel member.

6. The assembly of claim 4 wherein said light extracting deformities vary in density along a length of said panel member between said opposite ends.

7. The assembly of claim 4 wherein said light extracting deformities vary in size.

8. The assembly of claim 4 wherein said light extracting deformities vary in percent of coverage along a length of said panel member between said opposite ends.

9. The assembly of claim 4 wherein said light extracting deformities are shaped with no specific angles.

10. The assembly of claim 4 wherein said light extracting deformities are printed on said panel member.

11. The assembly of claim 4 wherein said light extracting deformities vary in shape.

12. The assembly of claim 1 wherein said light transition area includes a slot, cavity or opening in which said light source is snapped in place.

13. A light emitting panel assembly comprising a light emitting panel member having a greater width than thickness and opposite ends and sides and top and bottom surfaces, a light transition area located at one of said ends, and a plurality of light sources mounted to said light transition area, said panel member having a light input surface at said one end for receiving light from said light transition area, said light input surface having a cross sectional area extending the entire width and thickness of said panel member at said one end, and said light transition area having a light output surface of the same width and thickness as said light input surface at said one end and a reflective surface in close proximity to each of said light sources shaped to cause internal reflection of a portion of the light emitted from said light sources and redirect the internally reflected light into said light input surface at said one end to produce a uniform density of light across substantially the entire cross sectional area of said light input surface.

14. A light emitting panel assembly comprising a light emitting panel member having a greater width than thickness and opposite ends and sides and top and bottom surfaces, a light transition area located at one of said ends, and at least one light source mounted to said light transition area, said panel member having a light input surface at said one end for receiving light from said light transition area, said light input surface having a cross sectional area extending the entire width and thickness of said panel member at said one end, and said light transition area having a light output surface of the same width and thickness as said light input surface at said one end and a reflective surface in close proximity to said light source shaped to cause internal reflection of a portion of the light emitted from said light source and redirect the internally reflected light into said light input surface at said one end to produce a uniform density of light across substantially the entire cross sectional area of said light input surface, and a pattern of light extracting deformities on said panel member, said light extracting deformities having a density concentration for causing a substantially uniform light output from a light emitting surface on one of said top and bottom surfaces of said panel member, said pattern of light extracting deformities varying to compensate for a diffuser used with said panel member.

15. A light emitting panel assembly comprising a light emitting panel member having a greater width than thickness and opposite ends and sides and top and bottom surfaces, a light transition area located at one of said ends, and at least one light source mounted to said light transition area, said panel member having a light input surface at said one end for receiving light from said light transition area, said light input surface having a cross sectional area extending the entire width and thickness of said panel member at said one end, and said light transition area having a light output surface of the same width and thickness as said light input surface at said one end and a reflective surface in close proximity to said light source shaped to cause internal reflection of a portion of the light emitted from said light source and redirect the internally reflected light into said light input surface at said one end to produce a uniform density of light across substantially the entire cross sectional area of said light input surface, and a pattern of light extracting deformities in contact with said panel member, said light extracting deformities having a density concentration for causing a substantially uniform light output from a light emitting surface on one of said top and bottom surfaces of said panel member, said pattern of light extracting deformities being on a film.

16. The assembly of claim 15 wherein said film is molded to said panel member.

17. The assembly of claim 15 wherein said film is attached to said panel member.

18. A light emitting panel assembly comprising a light emitting panel member having a greater width than thickness and opposite ends and sides and top and bottom surfaces, a light transition area located at one of said ends, and at least one light source mounted to said light transition area, said panel member having a light input surface at said one end for receiving light from said light transition area, said light input surface having a cross sectional area extending the entire width and thickness of said panel member at said one end, and said light transition area having a light output surface of the same width and thickness as said light input surface at said one end and a reflective surface in close proximity to said light source shaped to cause internal reflection of a portion of the light emitted from said light source and redirect the internally reflected light into said light input surface at said one end of said panel member to produce a uniform density of light across substantially the entire cross sectional area of said light input surface, and a pattern of light extracting deformities on said panel member, said light extracting deformities having a density concentration for causing a substantially uniform light output from a light emitting surface on one of said top and bottom surfaces of said panel member, said light extracting deformities varying in color to provide different colored light output areas on said panel member.

19. A light emitting panel assembly comprising a light emitting panel member having a greater width than thickness and opposite ends and sides and top and bottom surfaces, a light transition area located at one of said ends, and at least one light source mounted to said light transition area, said panel member having a light input surface at said one end for receiving light from said light transition area, said light input surface having a cross sectional area extending the entire width and thickness of said panel member at said one end, and said light transition area having a light output surface of the same width and thickness as said light input surface at said one end and a reflective surface in close proximity to said light source shaped to cause internal reflection of a portion of the light emitted from said light source and redirect the internally reflected light into said light input surface at said one end to produce a uniform density of light across substantially the entire cross sectional area of said light input surface, and a pattern of light extracting deformities on said panel member, said light extracting deformities having a density concentration for causing a substantially uniform light output from a light emitting surface on one of said to p and bottom surfaces of said panel member, said light extracting deformities varying in index of refraction.

20. A light emitting panel assembly comprising a light emitting panel member having a greater width than thickness and opposite ends and sides and top and bottom surfaces, a light transition area located at one of said ends, and at least one light source mounted to said light transition area, said panel member having a light input surface at said one end for receiving light from said light transition area, said light input surface having a cross sectional area extending the entire width and thickness of said panel member at said one end, and said light transition area having a light output surface of the same width and thickness as said light input surface at said one end and a reflective surface in close proximity to said light source shaped to cause internal reflection of a portion of the light emitted from said light source and redirect the internally reflected light into said light input surface at said one end to produce a uniform density of light across substantially the entire cross sectional area of said light input surface, and multiple layers of light extracting deformities on one of said surface s of said panel member, said light extracting deformities having a density concentration for causing a substantially uniform light output from a light emitting surface on one of said surfaces of said panel member.

21. A light emitting panel assembly comprising a light emitting panel member having a greater width than thickness and opposite ends and sides and top and bottom surfaces, a light transition area located at one of said ends, and at least one light source mounted to said light transition area, said panel member having a light input surface at said one end for receiving light from said light transition area, said light input surface having a cross sectional area extending the entire width and thickness of said panel member at said one end, and said light transition area having a light output surface of the same width and thickness as said light input surface at said one end and a reflective surface in close proximity to said light source shaped to cause internal reflection of a portion of the light emitted from said light source and redirect the internally reflected light into said light input surface at said one end to produce a uniform density of light across substantially the entire cross sectional area of said light input surface, and a pattern of light extracting deformities on said panel member, said light extracting deformities having a density concentration for causing a substantially uniform light output from a light emitting surface on one of said top and bottom surfaces of said panel member, said light extracting deformities being printed on said panel member using strochastic print pattern techniques.

22. A light emitting panel assembly comprising a light emitting panel member having a greater width than thickness and opposite ends and sides and top and bottom surfaces, a light transition area located at one of said ends, and at least one light source mounted to said light transition area, said panel member having a light input surface at said one end for receiving light from said light transition area, said light input surface having a cross sectional area extending the entire width and thickness of said panel member at said one end, and said light transition area having a light output surface of the same width and thickness as said light input surface at said one end and a reflective surface in close proximity to said light source shaped to cause internal reflection of a portion of the light emitted from said light source and redirect the internally reflected light into said light input surface at said one end to produce a uniform density of light across substantially the entire cross sectional area of said light input surface, and a pattern of light extracting deformities on said panel member, said light extracting deformities having a density concentration for causing a substantially uniform light output from a light emitting surface on one of said top and bottom surfaces of said panel member, said light extracting deformities being printed on said panel member using frequency modulated half tone patterns.

23. A light emitting panel assembly comprising a light emitting panel member having a greater width than thickness and opposite ends and sides and top and bottom surfaces, a light transition area located at one of said ends, and at least one light source mounted to said light transition area, said panel member having a light input surface at said one end for receiving light from said light transition area, said light input surface having a cross sectional area extending the entire width and thickness of said panel member at said one end, and said light transition area having a light output surface of the same width and thickness as said light input surface at said one end and a reflective surface in close proximity to said light source shaped to cause internal reflection of a portion of the light emitted from said light source and redirect the internally reflected light into said light input surface at said one end to produce a uniform density of light across substantially the entire cross sectional area of said light input surface, and a pattern of light extracting deformities on said panel member, said light extracting deformities having a density concentration for causing a substantially uniform light output from a light emitting surface on one of said top and bottom surfaces of said panel member, said light extracting deformities being printed on said panel member using dot half tones.

24. A light emitting panel assembly comprising a light emitting panel member having a greater width than thickness and opposite ends and sides and top and bottom surfaces, a light transition area located at one of said ends, and at least one light source mounted to said light transition area, said panel member having a light input surface at said one end for receiving light from said light transition area, said light input surface having a cross sectional area extending the entire width and thickness of said panel member at said one end, and said light transition area having a light output surface of the same width and thickness as said light input surface at said one end and a reflective surface in close proximity to said light source shaped to cause internal reflection of a portion of the light emitted from said light source and redirect the internally reflected light into said light input surface at said one end to produce a uniform density of light across substantially the entire cross sectional area of said light input surface, and a pattern of light extracting deformities on said panel member, said light extracting deformities having a density concentration for causing a substantially uniform light output from a light emitting surface on one of said top and bottom surfaces of said panel member, said light extracting deformities varying in density across the width of said panel member.

25. A light emitting panel assembly comprising a light emitting panel member having a greater width than thickness and opposite ends and sides and top and bottom surfaces, a light transition area located at one of said ends, and at least one light source mounted to said light transition area, said panel member having a light input surface at said one end for receiving light from said light transition area, said light input surface having a cross sectional area extending the entire width and thickness of said panel member at said one end, and said light transition area having a light output surface of the same width and thickness as said light input surface at said one end and a reflective surface in close proximity to said light source shaped to cause internal reflection of a portion of the light emitted from said light source and redirect the internally reflected light into said light input surface at said one end of said panel member to produce a uniform density of light across substantially the entire cross sectional area of said light input surface, and a pattern of light extracting deformities on said panel member, said light extracting deformities having a density concentration for causing a substantially uniform light output from a light emitting surface on one of said top and bottom surfaces of said panel member, said light extracting deformities varying in percent of coverage across the width of said panel member.

* * * * *